United States Patent [19]

O'Brien et al.

[11] 4,390,517

[45] Jun. 28, 1983

[54] METHOD, COMPOSITION AND KIT FOR STABILIZING RADIOLABELED COMPOUNDS

[75] Inventors: Robert E. O'Brien, Belmont; Nathan R. Tzodikov, Milton, both of Mass.

[73] Assignee: New England Nuclear Corporation, Boston, Mass.

[21] Appl. No.: 178,609

[22] Filed: Aug. 15, 1980

Related U.S. Application Data

[63] Continuation-in-part of Ser. No. 105,272, Dec. 19, 1979.

[51] Int. Cl.³ .................... A61K 43/00; A61K 49/00; B65D 71/00
[52] U.S. Cl. .......................................... 424/1; 422/61; 424/9
[58] Field of Search ............... 424/1, 9, 12; 23/230 B; 422/61

[56] References Cited

U.S. PATENT DOCUMENTS

| | | | |
|---|---|---|---|
| 3,928,293 | 12/1975 | Crosby | 250/570.9 |
| 4,029,706 | 6/1977 | Crosby | 260/570.9 |
| 4,048,296 | 9/1977 | Wolfangel | 424/1 |
| 4,048,416 | 9/1977 | Axen et al. | 424/1 |
| 4,062,933 | 12/1977 | Wolfangel | 424/1 |
| 4,062,933 | 12/1977 | Wolfangel | 424/1 |
| 4,107,283 | 8/1978 | Pratt et al. | 424/1 |
| 4,107,867 | 8/1978 | Sultanian et al. | 424/1 |
| 4,112,064 | 9/1978 | Farrenkopf et al. | 424/1 |
| 4,115,540 | 9/1978 | Digenis et al. | 424/1 |
| 4,217,338 | 8/1980 | Quash | 424/1 |
| 4,229,427 | 10/1980 | Whitehouse | 424/1 |

FOREIGN PATENT DOCUMENTS

| | | | |
|---|---|---|---|
| 88780 | 12/1970 | German Democratic Rep. | 521/25 |
| 432218 | 6/1974 | U.S.S.R. | 521/25 |

OTHER PUBLICATIONS

Sorantin, Chemical Abstracts, vol. 81, 1974, Abstract No. 162498t.
Liebster et al., Rad. Biol., 1, 157, (1964).
Atomic Energy Review, 10, 3-66, (1972).
Stroh, Methoden der Organischen Chemie (Houben-Weyl), Ed., Muller et al., vol. IV/Ib, Oxidaion II, Georgthieme Verlag, (1975).
Encyclopedia of Chemical Technology, Kirk-Othmer, Interscience Publ., N.Y.
Merrifield, J. Am. Chem. Soc., 85,2149 (1963).
Crowley et al., Accts. Chem. Res., 9,135, (1976).
Stark, Biochemical Aspects of Reactions on Solid Supports, Academic Press, N.Y.

*Primary Examiner*—Christine M. Nucker
*Attorney, Agent, or Firm*—Sewall P. Bronstein; George W. Neuner

[57] ABSTRACT

A method of stabilizing a solution of a radiolabeled compound comprising adding to such solution a compound having a substantially insoluble backbone, to which has been bound a quaternary ammonium group; or a water soluble primary, secondary or tertiary aliphatic amine. The present invention also includes a solution of a radiolabeled compound maintained in contact with such a compound, and as an article of manufacture, a sealed vial containing such a solution.

35 Claims, No Drawings

METHOD, COMPOSITION AND KIT FOR STABILIZING RADIOLABELED COMPOUNDS

CROSS REFERENCE TO RELATED APPLICATION

This application is a continuation-in-part of Ser. No. 105,272, filed Dec. 19, 1979.

BACKGROUND OF THE INVENTION

1. Field of the Invention

This invention relates to the stabilization of radiolabeled compounds, such as amino acids and nucleosides, and more particularly, to stabilization of such compounds by the addition of soluble and insoluble compounds to solutions of radiolabeled compounds.

2. Description of the Prior Art

An increasing number of radiolabeled compounds are being used in research, for medical diagnosis, and various other areas. However, the radiolytic decomposition of such compounds has been a constant problem. Without the addition of some type of stabilizer, a solution of such a compound may become unusable due to decomposition within a matter of weeks or less. This radiolytic decomposition of such compounds has been studied extensively. For example, the radiation chemistry of amino acids is reviewed in an article by J. Liebster and J. Kopeldova, *Radiation Biol.*, 1, 157 (1964) and the self-decomposition of radioactivity lableled compounds is discussed in *Atomic Energy Review*, 10, 3-66 (1972), both incorporated herein by reference. While certain specific compounds have been suggested for stabilization, problems still exist. The latter article reviews the underlying causes and mechanisms of self-decomposition, "which are very complex and in some cases not well understood." (At p.3). After discussing the principal mechanisms by which decomposition occurs, the article notes generally at page 36 that buffers such as ammonium bicarbonate help to stabilize radiolabeled compounds, but care must be taken to insure that the buffer chosen does not interfere with the later use of the labeled compound. For example, phosphate buffers would interfere with phosphorylation reactions. Other compounds which have been suggested at various times are listed at page 35 and include benzyl alcohol, glycerol, cysteamine, and sodium formate. However each of these are said to suffer due to their difficulty of removal. Another compound mentioned is ethanol which is said to work with many compounds. However, ethanol sometimes actually sensitizes certain nucleosides to radiation decomposition and thus it has been found not to be a universal panacea. Furthermore, if it will interfere with the reaction in which the radiolabeled compound is to be used, the ethanol must be removed by evaporation which may also contribute to decomposition.

Various compounds are suggested in *Atomic Energy Review*, above, for stabilization of radiolabeled compounds prone to oxidation including antioxidants such as butylated-hydroxytoluene, butylated-hydroxyanisole and mercaptoethanol. While not mentioned for use with radiolabeled compounds, the inhibition of autoxidation generally by certain amines has also been described in the prior art. Recent reviews on the inhibition of autoxidation are "Autoxidation" by R. Stroh, p. 1049 in, *Methoden der Organischen Chemie* (Houben-Weyl), ed. E. Muller and O. Bayer Vol. IV/Ib Oxidation II., Georgthieme Verlag, 1975, and *Encyclopedia of Chemical Technology*, Kirk Othmer, Interscience Publishers, New York. The prior art teaches the utility of secondary dialkyl amines bearing full alpha-substitution (i.e. containing no hydrogens on the carbon atoms adjacent to the nitrogen) and secondary diarylamines (also without alpha-hydrogens) as antioxidants. However, the prior art does not teach the use of primary, secondary and tertiary amines, those containing alpha-hydrogens, in this regard and in fact suggests that they are not effective for this purpose. However such antioxidants have many of the same problems as other of the compounds discussed above, including in addition generally being insoluble in the solvents used to dissolve and store radiolabeled compounds for use in biological studies.

Accordingly, there has been a continuing need for alternatives to the stabilizers known in the prior art.

The synthesis and use of polystyrene supported reagents for solid phase peptide preparation is known in the prior art. R. B. Merrifield, *J. Am. Chem. Soc.*, 85, 2149 (1963); Crowley et al, *Accts. Chem. Res.*, 9, 135 (1976); G. R. Stark (1971), *Biochemical Aspects of Reactions on Solid Supports*, Academic Press, N.Y., U.S. Pat. Nos. 3,928,293 and 4,029,706 describe thiohydrocarbon polymers and their use as borane chelaters. However, neither the synthesis nor use of the insoluble compounds of the present invention are described in any of the above.

SUMMARY OF THE INVENTION

The present invention is a method of stabilizing a solution of a radiolabeled compound comprising adding to such solution a compound having a substantially insoluble backbone, preferably a resin, such as an ion exchange resin, to which has been bound a quaternary ammonium group; or a water soluble primary, secondary or tertiary aliphatic amine which does not interfere with the use contemplated for the particular radiolabeled compound so stabilized. The present invention also includes a solution of a radiolabeled compound maintained in contact with such a compound, and as an article of manufacture, a sealed vial containing such a solution.

DETAILED DESCRIPTION OF THE INVENTION

In accordance with the present invention it has been found that various amines and quaternary ammonium compounds stabilize solutions of radiolabeled compounds. A prior application, of which this is a continuation-in-part, describes the stabilization of radiolabeled compounds by maintaining a solution of such a labeled compound in contact with a compound having a quaternary ammonium group bound to a substantially insoluble backbone. Even before the earlier application was filed, the present inventors had discovered that certain soluble amines would act as stabilizers of radiolabeled compounds. That earlier application describes one specie of the present generic invention. While originally believed to not only stabilize solutions of radiolabeled compounds, but to do so without adulterating such solutions, further studies using both soluble amines and insoluble quaternary ammonium containing compounds have shown that such quaternary ammonium containing compounds stabilize such solutions at least in part by the release of soluble amines. For example, the polystyrene-divinyl benzene copolymer substituted by triethyl ammonium as described in Example VII below provides stabilization, at least in part, by the release of soluble triethyl amine, a tertiary aliphatic amine. At the same time, it has also been found that depending on how the radiolabeled compound is to be used, the presence of such soluble amines is compatible with the ultimate use for the labeled compound. While care must be exercised to insure that the particular stabilizer does not interfere with the ultimate use for the radiolabeled compound, it has been found that soluble amines are generally useful for stabilizing solutions of such radiolabeled compounds in the same manner as amines which are released into solution from insoluble substrates to which they have previously been bound. For the sake of convenience, the species of the generic invention will be described separately for the most part, although it should be recognized that all the species of the present invention stabilize, at least in part, by virtue of their presence in solution.

The substantially insoluble quaternary ammonium containing compounds of the present invention can be any of those well known in the prior art. A preferred class of such compounds is that prepared by attaching quaternary ammonium groups to an insoluble polystyrene-divinylbenzene copolymer backbone, e.g., a copolymer formed by copolymerizing about 1% to about 10% by weight of divinylbenzene with styrene. The preparation of such copolymers is well known in the prior art and they are sold commercially for use as anion exchange resins. Such commercially available copolymers are preferably treated by washing with ethanol and then methylene chloride, followed by drying before being employed to stabilize radiolabeled compounds.

The nitrogen of the quaternary ammonium group is preferably substituted by hydroxyalkyl or alkyl chains, preferably lower alkyl, and more preferably of from 1 to 5 carbon atoms.

The counterion (anion) of both the soluble and insoluble quaternary compounds of the present invention can be any of those known in the prior art which do not significantly detract from the stabilization provided by the quaternary ammonium group. Preferred counterions are halides and alkyl carboxylate ions of one to five carbon atoms, such as formate and acetate. A particularly preferred counterion is chloride.

Particularly preferred for use in the present invention are novel compounds prepared by attaching a sulfide or thiol group to the substantially insoluble stabilizing compounds described above. Preferred sulfide groups are those substituted by an alkyl group of one to five carbon atoms. Insoluble ammonium sulfide compounds have been found to be particularly effective in stabilizing solutions of radiolabeled compounds.

With respect to amines and quaternary ammonium compounds soluble in the aqueous solutions used to store radiolabeled compounds for biological use, it has been found that such compounds may be selected from the group consisting of:
(a) $RNH_2$,
(b) $RR^1NH$,
(c) $RR^1R^2N$,
(d) $R^3R^4N-R-NR^3R^4$, and
(e)

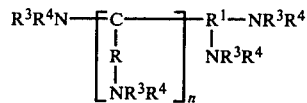

and quaternized salts thereof, wherein
R, $R^1$ and $R^2$ are the same or different and are alkyl, cycloalkyl, alkenyl, hydroxyalkyl, aminoalkyl, thioalkyl, carboxyalkyl, or keto alkyl or one to eight carbon atoms, or R and $R^1$ of $RR^1NH$ are combined to form a chain of four to six carbon atoms attached at each end to N, or one of the carbon atoms of the chain may be replaced by O or N;
$R^3$ and $R^4$ are the same or different and are hydrogen or R, $R^1$, or $R^2$; and
n is an integer between 0 and 1000.

Preferred soluble amines include triethylamine, tris (hydroxymethyl) methyl amine, hydroxyethylpiperazine ethyl sulfate, morpholine ethyl sulfate, and quaternary salts derived therefrom, particularly preferred such salts being triethylamine hydrochloride and tris (hydroxymethyl) methyl ammonium hydrochloride.

While any amount of the stabilizer compounds described above is beneficial in preventing the decomposition of radiolabeled compounds, in the case of the quaternary ammonium substantially insoluble stabilizers it is preferred that the nitrogen be in excess equivalents of between about $10^2$ and about $10^5$, more preferably between about $10^3$ and $10^4$, and most preferably about $10^4$. When a sulfide or thiol group is attached to the backbone, it is preferred that the sulfur be present in equivalent excesses between about $10^2$ and $10^5$, preferably between about $10^3$ and about $10^4$, and most preferably about $10^4$. By equivalent excess is meant, an excess of the respective atom, e.g., nitrogen, in the stabilizing compound over the equivalents of the radiolabeled compound. Similarly in the case of soluble compounds, it is preferred that the stabilizing compound be present at concentrations between about 1 millimolar through about one molar depending on the specific activity of the radiolabeled compound, the concentration of the radiolabeled compound in the solution, and the particular radioisotope being employed as the label. In general, it is preferred that the concentration of stabilizing agent be $10^3$ to $10^5$ times the concentration of labeled compound. For example a tritiated compound with a specific activity of 100 Ci/mMole would preferably contain between about 10 and about 20 mM concentration of amine; a $10^3$ excess. Similarly, if the label used is phosphorus-32 which might produce a specific activity of 1000 Ci/mMole, a one molar concentration of amine would be preferred, a $10^5$ excess.

In addition to the use of any of the above described amines alone, in some instances, it is preferred to use the soluble amines in combination. Preferred combinations are tris (hydroxymethyl) methyl ammonium hydrochloride and either ethylenediaminetetraacetic acid (EDTA) or diethylenetriaminepentaacetic acid (DETAPAC). Such combinations are particularly preferred for stabilizing the storage of nucleotides and preferably employed in a ratio of about 10:1 of the former to the latter with the overall ratio of labeled compound to stabilized compound being as above. EDTA and DETAPAC are also known to function as chelators of metal ions and thus cannot be used when the stabilized compound is to later be used in a reaction where chelation of metal ions must be avoided.

The method of the present invention can be used with any of the solvents typically used to store radiolabeled compounds such as water, ethanol, mixtures of water and ethanol in any ratio, benzene, hexane, dilute mineral and organic acids, and other such solvents employed in the prior art.

The present invention can be used to prevent the decomposition of radiolabeled compounds which have been labeled with any of the radionuclides used for such purposes, including tritium, carbon-14, phosphorus-32, phosphorus-33, sulfur-35, and the various radioisotopes of iodine, including iodine-125, and iodine-131.

The radiolabeled compound may be any of those subject to radiolytic decomposition, such as radiolabeled organic compounds. Examples of such organic compounds include amino acids such as lysine, tyrosine, phenylalanine, and tryptophan.

The stabilizing compounds are particularly effective with methionine and leucine. Other such organic compounds include peptides; nucleosides, such as thymidine and uridine; nucleotides, polynucleotides; lipids, steroids, and catecholamines.

Radiolabeled compounds are typically commercially distributed in closed vials containing a solution of the particular radiolabeled compound. Stabilizing compounds with an insoluble backbone can take various forms as long as they are maintained in contact with the solution of radiolabeled compound. An example of a possible form is solid beads which are added to a solution of the radiolabeled compound, in which case the solution would be removed from the stabilizing compound by decanting or withdrawing by means of a syringe. Another potential means of storage would be to provide the stabilizing compound in a form whereby the solution of the radiolabeled compound would be absorbed by the stabilizing compound. In such a case, the solution of radiolabeled compound would be eluted from the mass of stabilizing compound by use of a suitable solvent. Once separated, the solution of radiolabeled compound is used in the same manner as unstabilized solutions thereof. In the case of soluble amines, the stabilizing compound is simply added to a solution of the radiolabeled compound which is typically shipped in a sealed vial from which the stabilized compound is removed by withdrawing by means of a syringe.

The invention will be further clarified by a consideration of the following examples, which are intended to be purely exemplary of the use of the invention.

EXAMPLE I

Preparation of Polystyrene-divinylbenzene bound ammonium sulfide, chloride form

To a suspension of chloromethylated polystyrene copolymerized with 1% divinylbenzene (10 g, 42.5 milliequivalents chloride by analysis) in methylene chloride (200 ml) was added ethanethiol (15.7 ml, 213 mMol) and triethylamine (29.6 ml, 213 mMol). A slight yellow color began to develop after approximately 10 minutes and the mixture was allowed to stir for 60 hrs. under a nitrogen atmosphere. The resultant suspension was filtered through paper and continuously extracted with chloroform for 24 hrs., ethanol 3 hrs., then washed with chloroform (5×40 ml), ethanol (5×40 ml) and the white resin that remained was dried in a vacuum oven at 60° C./20 mm to leave 10 g of the ammonium sulfide polymer. The analysis of C, 71.18; H, 8.84; N, 2.15; S, 4.90; Cl, 5.26 indicates 1.53 mequivalents Sulfur/g, 1.53 mequivalents Nitrogen/g, and 1.48 mequivalents Chloride/g of polymer resin.

EXAMPLE II

Preparation of the Ammonium Sulfide Polymer in its acetate form

The ammonium chloride of Example I (3 g) was stirred with 1 N NaOH (100 ml) for 3 hours, filtered and washed three times successively with methylene chloride (50 ml) then ethanol (50 ml). The resultant resin was dried overnight at 23° C./20 mM to afford 2.7 g of a yellow product which analysed for C, 73.39; H, 8.83; N, 1.90; S, 4.78; Cl, 3.08. This analysis indicates 1.36 mequivalents Nitrogen/g, 1.49 mequivalents Sulfur/g, and 0.88 mequivalents Chloride/g of polymer resin.

The yellow product above was washed with 10% aqueous acetic acid (100 ml) then three times successively with methylene chloride (40 ml) followed by ethanol (40 ml). The resultant white product was dried at 23°/20 mM to afford Example II as the acetate 2.7 g.

The following Examples demonstrate the use of various insoluble quaternary ammonium containing compounds and soluble amines to stabilize various radiolabeled compounds. The analytical method employs liquid chromatography for separation followed by post column radioactivity quantitization. The values given are an average of three separate determinations from triplicate packagings.

EXAMPLES III-V

The following examples detail the storage of tritium-labeled methionine in aqueous ethanol solution with an initial radiochemical purity of 98% with the stabilizers of Examples I and II. The average change in purity is based upon three individual determinations.

| Ex. | Stabilizer | Number of Days Stored | Average Change in Purity (%) | Molar Excess |
|-----|-----------|-----------------------|------------------------------|--------------|
|     | None      | 47                    | 6                            |              |
|     |           | 62                    | 11                           |              |
|     |           | 87                    | 13                           |              |
|     |           | 118                   | 19                           |              |
| III | Compound of Ex. I | 47           | 1                            |              |
|     |           | 62                    | 3                            | $1.2 \times 10^3$ |
|     |           | 87                    | 4                            | of Sulfur    |
|     |           | 118                   | 11                           | and Nitrogen |
| IV  | Compound of Ex. I | 48           | 0                            | $8.7 \times 10^3$ |
|     |           | 62                    | 0                            | of Sulfur    |
|     |           | 87                    | 0                            | and Nitrogen |
|     |           | 119                   | 3                            |              |
| V   | Compound of Ex. II | 47          | 2                            | $1.2 \times 10^3$ |
|     |           | 62                    | 4                            | of Sulfur    |
|     |           | 87                    | 5                            | and Nitrogen |
|     |           | 118                   | 12                           |              |

EXAMPLE VI

An aqueous solution of methionine having an initial purity of 93% was divided into equal parts. One part was stored without any stabilizer, while the other part was stored over 4.5×10³ molar excess of the compound of Example I. After 36 days the change in radiochemical purity was 75% and 12% respectively. After 66 days the change in radiochemical purity was 85% and 19% respectively, and the biological activity of the two solutions was tested by attempting to use the stored solutions for protein translation. The solution of methionine stored without any stabilizer failed to translate effectively, whereas the solution stored over stabilizer underwent efficient protein translation.

| Ex. | Stabilizer | Number of Days Stored | Average Change in Purity (%) | Molar Excess |
|---|---|---|---|---|
| | None | 36 | 75 | |
| | | 66 | 85 | |
| VI | Compound of Ex. I | 36 | 12 | 4.5 × 10³ of Sulfur and Nitrogen |
| | | 66 | 19 | |

EXAMPLES VII AND VIII

Examples VII and VIII illustrate the use of the present invention with the stabilizer of Example I and polystyrenedivinyl benzene copolymer substituted by triethyl ammonium with chloride as the counterion (TEAC) to stabilize a solution of tritium labeled lysine with a starting purity of 98.5%.

| Ex. | Stabilizer | Number of Days Stored | Average Change in Purity (%) | Molar Excess |
|---|---|---|---|---|
| | None | 34 | 3.0 | |
| | | 70 | 6.0 | |
| VII | TEAC | 34 | 0.5 | 1.5 × 10³ of Sulfur and Nitrogen |
| | | 70 | 1.5 | |
| VIII | Compound of Ex. 1 | 34 | 0.5 | 1.5 × 10³ of Sulfur and Nitrogen |
| | | 70 | 1.5 | |

EXAMPLES IX-XII

Examples IX-XII illustrate the use of the present invention to stabilize a radiolabeled nucleoside, tritium-labeled thymidine. Examples IX and X employ the stabilizer of Example I, whereas Examples XI and XII employ a commercially available polystyrenedivinyl benzene copolymer anion exchange resin to which has been bound a trimethyl ammounium group with chloride as the counterion (TMAC) in accordance with the present invention.

| Ex. | Stabilizer | Number of Days Stored | Average Change in Purity (%) | Molar Excess |
|---|---|---|---|---|
| | None | 14 | 3 | |
| | | 22 | 7 | |
| | | 29 | 7 | |
| IX | Compound of Ex. I | 14 | 0 | 10⁴ Nitrogen and Sulfur |
| | | 22 | 5 | |
| | | 29 | 3 | |
| X | Compound of Ex. 1 | 14 | 0 | 2 × 10⁴ Nitrogen and Sulfur |
| | | 22 | 2 | |
| | | 29 | 2 | |
| XI | TMAC | 14 | 0 | 10⁴ Nitrogen |
| | | 22 | 1 | |
| | | 29 | 2 | |
| XII | TMAC | 14 | 0 | 2 × 10⁴ Nitrogen |
| | | 22 | 3 | |
| | | 29 | 1 | |

EXAMPLES XIII-XV

The following examples detail the storage of tritium labeled methionine (80 Ci/mMol) in aqueous 70% ethanol solution with an initial radiochemical purity of 98% to give 1 mCi/ml at −20° C. with amines as indicated.

Example XIII

| Stabilizer | Number of Days Stored | Average Change in Purity (%) | Molarity |
|---|---|---|---|
| None | 79 | 12 | — |
| Cyclohexyl isopropyl amine | 79 | 5 | 20 mM |

Example XIV

| Stabilizer | Number of Days Stored | Average Change in Purity (%) | Molarity |
|---|---|---|---|
| None | 45 | 6 | |
| | 80 | 9 | |
| | 114 | 12 | |
| 1,5-Diaminopentane | 50 | 1 | 20 mMolar |
| | 84 | 1 | |
| | 114 | 2 | |
| 1,6-Diaminohexane | 51 | 1 | 20 mMolar |
| | 84 | 2 | |
| | 114 | 2 | |

Example XV

| Stabilizer | Number of Days Stored | Average Change in Purity (%) | Molarity |
|---|---|---|---|
| None | 45 | 6 | |
| | 80 | 9 | |
| | 114 | 12 | |
| triethyl amine | 49 | 1 | 0.7 mM |
| | 83 | 4 | |
| | 114 | 5 | |

EXAMPLE XVI

The following example details the storage of tritium labeled methionine (80 Ci/mMol) in water with an initial radiochemical purity of 94% to give a concentration of 1 mCi/ml at 4° C. with the amine as indicated.

Example XVI

| Stabilizer | Number of Days Stored | Average Change in Purity (%) | Molarity |
|---|---|---|---|
| None | 6 | 21 | |
| | 16 | 35 | |
| | 22 | 46 | |
| | 30 | 57 | |
| | 51 | 72 | |
| Triethylamine | 6 | 3 | 10mMolar |
| | 16 | 6 | |
| | 22 | 7 | |
| | 30 | 8 | |
| | 51 | 11 | |

EXAMPLES XVII-XVIII

The following examples detail the storage of sulfur-35 labeled methionine (1000 Ci/mMol) in water with an initial radiochemical purity of 95% to give a concentration of 10 mCi/ml with the amines as indicated. Examples XVII and XVIII were stored at 4° C. while Example XIX was stored at −20° C. Tris refers to tris (hydroxymethyl) methyl amine.

Example XVII

| Stabilizer | Number of Days Stored | Average Change in Purity (%) | Molarity |
|---|---|---|---|
| None | 1 | 17 | |
| | 4 | 37 | |
| | 8 | 57 | |
| triethyl amine | 2 | 14 | 1 molar |
| | 4 | 14 | |
| | 8 | 16 | |
| | 15 | 19 | |
| triethyl amine | 2 | 15 | 100mMolar |
| | 4 | 16 | |
| | 8 | 20 | |
| | 15 | 33 | |

Example XVIII

| Stabilizer | Number of Days Stored | Average Change in Purity (%) | Molarity |
|---|---|---|---|
| None | 1 | 8 | |
| | 2 | 15 | |
| | 5 | 33 | |
| | 18 | 86 | |
| Tris (as free base) | 1 | 4 | 1 Molar |
| | 2 | 6 | |
| | 5 | 12 | |
| | 18 | 35 | |

Example XIX

| Stabilizer | Number of Days Stored | Average Change in Purity (%) | Molarity |
|---|---|---|---|
| None | 3 | 6 | |
| | 9 | 11 | |
| Tris.HCl | 3 | 0 | 10mMolar |
| | 9 | 4 | |

EXAMPLE XX

Example XX details the storage of tritium labeled Enkephalin (5-L-methionine) (30 Ci/mMol) in an aqueous solution containing 70% ethanol with an initial radiochemical purity of 98% to give a concentration of 1 mCi/ml at −20° with various amines as indicated.

| Stabilizer | Number of Days Stored | Average Change in Purity (%) | Molarity |
|---|---|---|---|
| None | 26 | 13 | |
| Triethylamine | 26 | 0 | 33 mMolar |
| Hepes (hydroxyethyl piperazine ethyl sulfate) | 26 | 4 | 3 mMolar |

EXAMPLE XXI

Example XXI details the storage of tritium labeled chemotactic peptide (57 Ci/mMol) in an aqueous solution containing 50% ethanol with an initial radiochemical purity of 99% to give a concentration of 1 mCi/ml at −20° C. with polylysine.hydrobromide (av. M.W. 20,000).

| Stabilizer | Number of Days Stored | Average Change in Purity (%) | Molarity |
|---|---|---|---|
| None | 54 | 4 | |
| | 216 | 13 | |
| Polylysine.HBr | 54 | 1 | 1 mMolar |
| | 216 | 5 | |

EXAMPLES XXII–XXIII

Examples XXII and XXIII detail the storage of deoxyguanosine-5′-triphosphate labeled with phosphate-32 (660 Ci/mMol) in water with an initial radiochemical purity of 95% to give a concentration of 10 mCi/ml at −30° C. with the amines indicated. EDTA is an abbreviation for ethylene diamine tetracetic acid.

Example XXII

| Stabilizer | Number of Days Stored | Average Change in Purity (%) | Molarity |
|---|---|---|---|
| None | 9 | 9 | — |
| Tris (free base) | 9 | 5 | 800 mMolar |
| Tris.HCl | 9 | 5 | 800 mMolar |
| Triethylamine | 2 | 3 | 800 mMolar |

Example XXIII

| Stabilizer | Number of Days Stored | Average Change in Purity (%) | Molarity |
|---|---|---|---|
| None | 10 | 14 | — |
| Tris.HCl | 10 | 7 | 50 mMolar |
| Tris.HCl | 10 | 8 | 10 mMolar |
| EDTA | 10 | 7 | 1 mMolar |
| Tris.HCl/EDTA | 10 | 3 | 10mM/1mM |

EXAMPLE XXIV

Example XXIV details the storage of labeled Adenosine-5′-triphosphate labeled with phosphorus-32 (8100 Ci/mMol) in water at an initial radiochemical purity of 97% to give a concentration of 3 mCi/ml at −30° C. with triethylamine.

| Stabilizer | Number of Days Stored | Average Change in Purity (%) | Molarity |
|---|---|---|---|
| None | 13 | 7 | — |
| Triethylamine | 17 | 6 | 4 mMolar |
| Triethylamine | 17 | 3 | 40 mMolar |
| Triethylamine | 13 | 0 | 400 mMolar |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. In a kit comprising a container of a solution of a radiolabeled organic compound that is subject to radiolytic degradation during storage and shipment of the kit, the improvement which consists of adding a non-radiolabeled stabilizing compound to said solution for stabilizing said radiolabeled organic compound against radiolytic degradation during storage and shipment of said kit; said stabilizing compound being a water soluble amine having at least one alpha hydrogen on a carbon atom adjacent a nitrogen atom selected from the group consisting of:

(a) $RNH_2$,
(b) $RR^1NH$,
(c) $RR^1R^2N$, and
(d) $R^3R^4N-R-NR^3R^4$, or quaternary salts thereof wherein R, $R^1$ and $R^2$ are the same or different and are alkyl, cycloalkyl, alkyenl, hydroxyalkyl, aminoalkyl, thioalkyl, carboxyalkyl, or keto alkyl of one to eight carbon atoms, or R and $R^1$ of $RR^1NH$ are combined to form a chain of four to six carbon atoms attached at each end to N, or one of the carbon atoms of the chain may be replaced by O or N; and $R^3$ and $R^4$ are the same or different and are hydrogen or R, $R^1$ and $R^2$;

wherein the stabilizing compound is not the unlabeled form of the radiolabeled compound;

provided that when said stabilizing compound is ethylene diaminetetraacetic acid, a second stabilizing compound as defined is added to said solution.

2. A kit as claimed in claim 1 wherein said radiolabeled compound is a radiolabeled amino acid.

3. A kit as claimed in claim 1 wherein R, $R^1$, and $R^2$ are the same or different and are lower alkyl or hydroxyalkyl of one to four carbon atoms; and $R^3$ and $R^4$ are the same or different and are hydrogen, lower alkyl or hydroxyalkyl of one to four carbon atoms.

4. A kit as claimed in claim 1 wherein said stabilizing compound contains a quaternary ammonium and the counterion of said quaternary ammonium is halide or a lower alkyl carboxylate anion.

5. A kit as claimed in claim 1 wherein R,$R^1$, and $R^2$ are the same or different and are lower alkyl, hydroxyalkyl, or carboxyalkyl of one to four carbon atoms; and $R^3$ and $R^4$ are the same or different and are hydrogen, lower alkyl, hydroxyalkyl, or carboxyalkyl of one to four carbon atoms.

6. A kit as claimed in claim 1 wherein said stabilizing compound is selected from the group consisting of triethyl amine, tris (hydroxymethyl) methyl amine, and quaternary salts thereof; hydroxyethylpiperazine ethyl sulfate, and morpholine ethyl sulfate.

7. A kit as claimed in claim 1 wherein said stabilizing compound is cyclohexyl isopropyl amine; 1,5-diaminopentane; 1,6-diaminohexane; polylysine; or salts thereof.

8. A kit as claimed in claim 1 wherein the soluble amine is present at a concentration between about 0.001 and about 1 molar.

9. A kit as claimed in claim 1 wherein the ratio of the concentration of said radiolabeled compound to the concentration of said soluble amine is between about $1:10^3$ and about $1:10^5$.

10. A kit as claimed in claim 9 wherein said ratio is about 1:1000.

11. A kit as claimed in claim 1 wherein the solvent of said solution is water, ethanol, a mixture of water and ethanol, benzene, hexane, a dilute mineral acid, or a dilute organic acid.

12. A kit as claimed in claim 1 wherein the radionuclide of said radiolabeled compound is tritium, carbon-14, phosphorus-32, phosphorus-33, sulfur-35, iodine-125, or iodine-131.

13. A kit as claimed in claim 1 wherein said radiolabeled compound is stabilized by tris (hydroxmethyl) methyl amine hydrochloride and ethylene diamine tetraacetic acid in a molar ratio of about 10:1, respectively.

14. A method of stabilizing a solution of a radiolabeled organic compound that is subject to radiolytic degradation against such degradation during storage and shipment, of said radiolabeled organic compound, said method comprising adding to said solution a stabilizing compound, which is not radiolabeled, selected from a water soluble amine having at least one alpha hydrogen on a carbon atom adjacent a nitrogen atom selected from the group consisting of:

(a) $RNH_2$,
(b) $RR^1_{NH}$,
(c) $RR^1R^2N$, and
(d) $R^3R^4N-R-NR^3R^4$, or quaternized salts thereof, wherein:

R, $R^1$ and $R^2$ are the same or different and are alkyl, cycloalkyl, alkenyl, hydroxyalkyl, aminoalkyl, thioalkyl, carboxyalkyl or keto alkyl of one to eight carbon atoms, or R and $R^1$ of $RR^1NH$ are combined to form a chain of four to six carbon atoms attached at each end to N, or one of the carbon atoms of the chain may be replaced by O or N; and $R^3$ and $R^4$ are the same or different and are hydrogen or R, $R^1$, or $R^2$; wherein the stabilizing compound is not the unlabeled form of the radiolabeled compound;

with the proviso that when said stabilizing compound is ethylene diaminetetraacetic acid, a second stabilizing compound is added to said solution.

15. A method as claimed in claim 14 wherein said radiolabeled compound is a radiolabeled amino acid.

16. A method as claimed in claim 14 wherein said stabilizing compound contains a quaternary ammonium and the counterion of said quaternary ammonium is halide or a lower alkyl carboxylate anion.

17. A method as claimed in claim 14 wherein R,$R^1$, and $R^2$ are the same or different and are lower alkyl, hydroxyalkyl, or carboxyalkyl of one to four carbon atoms; and $R^3$ and $R^4$ are the same or different and are hydrogen, lower alkyl, hydroxyalkyl, or carboxyalkyl of one to four carbon atoms.

18. A method as claimed in claim 14 wherein said stabilizing compound is selected from the group consisting of triethyl amine, tris (hydroxymethyl) methyl amine, and quaternary salts thereof; hydroxyethylpiperazine ethyl sulfate, and morpholine ethyl sulfate.

19. A method as claimed in claim 14 wherein said stabilizing compound is cyclohexyl isopropyl amine; 1,5-diaminopentane; 1,6-diaminohexane; polylysine; ethylene diamine tetraacetic acid; or salts thereof.

20. A method as claimed in claim 14 wherin the soluble amine is present at a concentration between about 0.001 and about 1 molar.

21. A method as claimed in claim 14 wherein the ratio of the concentration of said radiolabeled compound to the concentration of said soluble amine is between about $1:10^2$ and about $1:10^5$.

22. A method as claimed in claim 21 wherein said ratio is about 1:100.

23. A method as claimed in claim 14 wherein the solvent of said solution is water, ethanol, a mixture of water and ethanol, benzene, hexane, a dilute mineral acid, or a dilute organic acid.

24. A method as claimed in claim 14 wherein the radionuclide of said radiolabeled compound is tritium, carbon-14, phosphorus-32, phosphorus-33, sulfur-35, iodine-125, or iodine-131.

25. A method as claimed in claim 14 wherein said radiolabeled compound is stabilized by tris (hydroxymethyl) methyl amine hydrochloride and ethylene diamine tetraacetic acid in a molar ratio of about 10:1, respectively.

26. In a kit comprising at least one container of a solution of a radiolabeled organic compound that is subject to radiolytic degradation during storage and shipment, the improvement wherein a stabilizing compound is added to said solution for stabilizing said radiolabeled organic compound against radiolytic degradation during storage and shipment; said stabilizing compound consisting of a non-radiolabeled, water-soluble amine, having at least one alpha hydrogen on a carbon atom adjacent to the nitrogen atom, $RNH_2$, wherein R is alkyl, cycloalkyl, alkenyl, hydroxyalkyl, aminoalkyl, thioalkyl, carboxyalkyl, or keto alkyl of one to eight carbon atoms, wherein the stabilizing compound is not the unlabeled form of the radiolabeled compound.

27. A method for stabilizing a solution of a radiolabeled organic compound that is subject to radiolytic degradation during storage and shipment against such degradation, said method comprising adding to said solution a stabilizing compound consisting of a non-radiolabeled, water-soluble amine having at least one alpha hydrogen on a carbon atom adjacent to the nitrogen atom, $RNH_2$, wherein R, is alkyl, cycloakyl, alkenyl, hydroxyalkyl, aminoalkyl, thioalkyl, carboxalkyl, or keto alkyl of one to eight carbon atoms, wherein the stabilizing compound is not the unlabeled form of the radiolabeled compound.

28. In a kit comprising at least one container of a solution of a radiolabeled organic compound that is subject to radiolytic degradation during storage and shipment, the improvement wherein a stabilizing compound is added to said solution for stabilizing said radiolabeled organic compound against radiolytic degradation during storage and shipment; said stabilizing compound consisting of a non-radiolabeled, water-soluble amine having at least one alpha hydrogen on a carbon atom adjacent to a nitrogen atom, $RR^1NH$, wherin R and $R^1$ are independently alkyl, cycloalkyl, alkenyl hydroxyalkyl, thioalkyl, carboxyalkyl, or keto alkyl of one to eight carbon atoms, or R and $R^1$ of $RR^1NH$ are combined to form a chain of four to six carbon atoms attached at each end to N, or one of the carbon atoms of the chain may be replaced by O or N, wherein the stabilizing compound is not the unlabeled form of the radiolabeled compound.

29. A method for stabilizing a solution of a radiolabeled organic compound that is subject to radiolytic degradation during storage and shipment against such degradation, said method comprising adding to said solution a stabilizing compound consisting of a non-radiolabeled water-soluble amine having at least one alpha hydrogen on a carbon atom adjacent to a nitrogen atom, $RR^1NH$, wherein R and $R^1$ are independently alkyl, cycloalkyl, alkenyl, hydroxyalkyl, thioalkyl, carboxyalkyl, or keto alkyl of one to eight carbon atoms, or R and $R^1$ of $RR^1NH$ are combined to form a chain of four to six carbon atoms attached at each end to N, or one of the carbon atoms of the chain may be replaced by O or N, wherein the stabilizing compound is not the unlabeled form of the radiolabeled compound.

30. In a kit comprising at least one container of a solution of a radiolabeled organic compound that is subject to radiolytic degradation during storage and shipment, the improvement wherein a stabilizing compound is added to said solution for stabilizing said radiolabeled organic compound against radiolytic degradation during storage and shipment; said stabilizing compound consisting of a non-radiolabeled water-soluble amine, $RR^1R^2N$, wherein R, $R^1$ and $R^2$ are each independently alkyl, cycloalkyl, alkenyl, hydroxyalkyl, aminoalkyl, thioalkyl, or keto alkyl of one to eight carbon atoms, wherein the stabilizing compound is not the unlabeled form of the radiolabeled compound.

31. A method for stabilizing a solution of a radiolabeled organic compound that is subject to radiolytic degradation during storage and shipment against such degradation, said method comprising adding to said solution a stabilizing compound consisting of a non-radiolabeled, water-soluble amine, $RR^1R^2N$, wherein R, $R^1$ and $R^2$ are each independently alkyl, cycloalkyl, alkenyl, hydroxyalkyl, aminoalkyl, thioalkyl, carboxyalkyl, or keto alkyl of one to eight carbon atoms, wherein the stabilizing compound is not the unlabeled form of the radiolabeled compound.

32. In a kit comprising at least one container of a solution comprising a radiolabeled organic compound that is subject to radiolytic degradation during shipment and storage, the improvement wherein a stabilizing compound is added to said solution for stabilizing said radiolabeled organic compound against said degradation; said stabilizing compound consisting of a non-radiolabeled, water-soluble secondary amine, having at least one alpha hydrogen on a carbon atom adjacent to a nitrogen atom, wherein one N-substituent is an hydroxyalkyl group having one to eight carbon atoms and the other N-substituent is selected from an alkyl, cycloalkyl, alkenyl, hydroxyalkyl, thioalkyl, carboxyalkyl, or keto alkyl group having one to eight carbon atoms, or the substituents are taken together to form a heterocyclic ring containing four to six carbon atoms and the nitrogen atom of said secondary amine wherein one of the carbon atoms can be O or N, wherein the stabilizing compound is not the unlabeled form of the radiolabeled compound.

33. A kit in accord with claim 32, wherein said other N-substituent is carboxyalkyl.

34. A method for stabilizing a solution comprising a radiolabeled organic compound that is subject to radiolytic degradation during storage and shipment against such degradation, said method comprising adding to said solution a stabilizing compound consisting of a non-radiolabeled, water-soluble, secondary amine having at least one alpha hydrogen on a carbon atom adjacent to a nitrogen atom, wherein one N-substituent is an hydroxyalkyl group having one to eight carbon atoms and the other N-substituent is selected from an alkyl, cycloalkyl, alkenyl, hydroxyalkyl, thioalkyl, carboxyalkyl or keto alkyl group having one to eight carbon atoms, or the substituents are taken together to form a heterocyclic ring containing four to six carbon atoms and the nitrogen atom of said secondary amine and wherein one of the carbon atoms can be O or N, wherein the stabilizing compound is not the unlabeled form of the radiolabeled compound.

35. The method of claim 34 wherein said other N-substituent is carboxyalkyl.

* * * * *